(12) United States Patent
Srinivas et al.

(10) Patent No.: US 9,174,919 B2
(45) Date of Patent: Nov. 3, 2015

(54) PROCESS FOR PREPARING BIODEGRADABLE LUBRICANT BASE OILS

(71) Applicant: Council of Scientific and Industrial Research, New Delhi (IN)

(72) Inventors: Darbha Srinivas, Pune (IN); Mehejabeen Kotwal, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/403,073

(22) PCT Filed: May 22, 2013

(86) PCT No.: PCT/IN2013/000330
§ 371 (c)(1),
(2) Date: Nov. 21, 2014

(87) PCT Pub. No.: WO2013/175509
PCT Pub. Date: Nov. 28, 2013

(65) Prior Publication Data
US 2015/0148554 A1    May 28, 2015

(30) Foreign Application Priority Data

May 22, 2012 (IN) .......................... 1558/DEL/2012

(51) Int. Cl.
*C07C 51/00* (2006.01)
*C07C 67/08* (2006.01)
*B01J 27/16* (2006.01)
*B01J 31/06* (2006.01)
*B01J 31/16* (2006.01)
*B01J 31/18* (2006.01)
*C07C 67/03* (2006.01)
*C11C 3/00* (2006.01)
*C11C 3/02* (2006.01)
*C11C 3/04* (2006.01)
*C11C 3/06* (2006.01)
*B01J 31/02* (2006.01)

(52) U.S. Cl.
CPC .................. *C07C 67/08* (2013.01); *B01J 27/16* (2013.01); *B01J 31/0275* (2013.01); *B01J 31/069* (2013.01); *B01J 31/1691* (2013.01); *B01J 31/185* (2013.01); *C07C 67/03* (2013.01); *C11C 3/003* (2013.01); *C11C 3/02* (2013.01); *C11C 3/04* (2013.01); *C11C 3/06* (2013.01); *B01J 2231/49* (2013.01); *B01J 2531/005* (2013.01); *B01J 2531/48* (2013.01)

(58) Field of Classification Search
CPC ............ C11C 3/06; C11C 3/04; C11C 3/003; C11C 3/02; C11C 3/025; C07C 67/03; C07C 67/08; C10M 2207/282; C08G 63/20; C08G 63/85; A61K 9/02; B32B 17/10605

USPC .......................................... 554/168, 172, 173
See application file for complete search history.

(56) References Cited

U.S. PATENT DOCUMENTS

| 7,968,504 | B2 | 6/2011 | Mosier et al. |
| 8,058,217 | B2 | 11/2011 | Suda et al. |
| 8,101,560 | B2 | 1/2012 | Choo et al. |
| 8,124,801 | B2 | 2/2012 | Srinivas et al. |
| 8,168,572 | B2 | 5/2012 | Thoen et al. |
| 2007/0004599 | A1 | 1/2007 | Darbha et al. |
| 2008/0257781 | A1 | 10/2008 | Lecocq et al. |

FOREIGN PATENT DOCUMENTS

| EP | 1733788 | 12/2006 |
| WO | WO-2012/114357 | 8/2012 |
| WO | WO-2013/175509 | 11/2013 |

OTHER PUBLICATIONS

"International Application No. PCT/IN2013/000330, Article 19 Amendment filed Dec. 6, 2013", 11 pgs.
"International Application No. PCT/IN2013/000330, International Search Report mailed Oct. 9, 2013", 4 pgs.
Bossaert, W. D., et al., "Mesoporous Sulfonic Acids as Selective Heterogeneous Catalysts for the Synthesis of Monoglycerides", Journal of Catalysis, 182(1), 156-164 (1999), (Feb. 15, 1999).
Clearfield, Abraham, et al., "Synthesis and Stability of Mixed Ligand Zirconium Phosphonate Layered Compounds", Journal of Solid State Chemistry, vol. 117, Issue 2, Jul. 1995, pp. 275-289.
Diaz, L., et al., "Influence of the alkyl chain length of HSO3-R-MCM-41 on the esterification of glycerol with fatty acids", Micropor. Mesopor. Mat. 80, 33-42, (2005).
Lanari, Daniela, et al., "New zirconium hydrogen phosphate alkyl and/or aryl phosphonates with high surface area as heterogeneous Brnsted acid catalysts for aza-Diels-Alder reaction in aqueous medium", Journal of Catalysis, vol. 277, Issue 1, Jan. 3, 2011, pp. 80-87.

(Continued)

*Primary Examiner* — Deborah D Carr
(74) *Attorney, Agent, or Firm* — Schwegman Lundberg & Woessner, P.A.

(57) ABSTRACT

The invention discloses an improved process for preparing fatty acid esters with 100 mol % selectivity suitable as biodegradable lubricant base oils, comprising contacting a fatty compound with an alcohol in presence of a solid, phosphonate catalyst having molecular formula: $M(X)_{2-n}Y_n \cdot mH_2O$ where X refers to phenyl phosphonate, Y refers to $HPO_4^{2-}$ or $HPO_3^{2-}$, M refers to a metal or metalloid ion preferably taken from the group consisting of Zr, Zn, Cd, Al, Sn, La and Ce, the value of n varies from 0.2 to 1.8 and the value of m varies from 0 to 5, wherein the fatty compound is a fatty acid or fatty acid methyl or ethyl ester or vegetable oil or animal fat or their mixture thereof and alcohol is a monohydric alcohol with 6 to 22 carbon atoms or a polyol with at least two hydroxyl groups.

10 Claims, No Drawings

(56) References Cited

OTHER PUBLICATIONS

Masood, Hassan, et al., "Synthesis and characterization of calcium methoxide as heterogeneous catalyst for trimethylolpropane esters conversion reaction", Applied Catalysis A: General, Applied Catalysis A: General 425-426 (2012) 184-190, (Mar. 21, 2012).

Nakamura, Kayoko, et al., "Intercalation of n-Alkylamines and n-Alkyldiamines into ?-Zirconium Phenylphosphonate Phosphate", Journal of inclusion phenomena and molecular recognition in chemistry, Aug. 1998, vol. 31, Issue 4, pp. 351-355.

Oh, Jinho, et al., "Synthesis of biolubricants using sulfated zirconia catalysts", Applied Catalysis A: General 455 (2013) 164-171, (Jan. 27, 2013).

Pérez-Pariente, Joaqu'in, et al., "Selective synthesis of fatty monoglycerides by using functionalised mesoporous catalysts", Applied Catalysis A: General 254 (2003) 173-188, (Apr. 7, 2003).

Pouilloux, Y., et al., "Reaction of glycerol with fatty acids in the presence of ion-exchange resins: Preparation of monoglycerides", J Mol Catal A-Chem. Dec. 15, 1999; 149 (1-2): 243-254.

Satyarthi, Jitendra Kumar, "Factors Influencing the Kinetics of Esterification of Fatty Acids over Solid Acid Catalysts", Energy Fuels 2011, 25(9), 4106-4122, (Sep. 15, 2011), 7 pgs.

Varhadi, Poonam, et al., "Zirconium phenyl phosphonate phosphite as a highly active, reusable, solid acid catalyst for producing fatty acid polyol esters", Applied Catalysis A: General, vols. 462-463, Jul. 10, 2013, pp. 129-136, 462-463.

Wang, J. Don, et al., "Preparation of layered zirconium phosphonate/phosphate, zirconium phosphonate/phosphite and related compounds", Materials Chemistry and Physics, vol. 35, Issues 3-4, Oct. 1993, pp. 208-216.

PROCESS FOR PREPARING BIODEGRADABLE LUBRICANT BASE OILS

PRIORITY CLAIM TO RELATED APPLICATIONS

This application is a U.S. national stage application filed under 35 U.S.C. §371 from International Application Serial No. PCT/IN2013/000330, which was filed May 22, 2013, and published as WO 2013/175509 on Nov. 28, 2013, and which claims priority to India Application No. 1558/DEL/2012, filed May 22, 2012, which applications and publication are incorporated by reference as if reproduced herein and made a part hereof in their entirety, and the benefit of priority of each of which is claimed herein.

FIELD OF THE INVENTION

The present invention relates to a process for preparing biodegradable lubricant base oils. Particularly, the present invention relates to an improved process for preparing fatty acid esters suitable as biodegradable lubricant base oils, comprising contacting a fatty compound with an alcohol in the presence of a solid phosphonate catalyst having molecular formula:

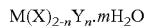
$$M(X)_{2-n}Y_n \cdot mH_2O$$

where X refers to phosphonate, Y refers to $HPO_4^{2-}$ or $HPO_3^{2-}$, M refers to a metal or metalloid ion preferably from the group consisting of Zr, Zn, Cd, Al, Sn, La and Ce, the value of n varies from 0.2 to 1.8 and the value of m varies from 0 to 5, wherein the fatty compound is a fatty acid or fatty acid methyl or ethyl ester or vegetable oil or their mixture thereof and alcohol is a monohydric alcohol with 6 to 22 carbon atoms or a polyol.

BACKGROUND OF THE INVENTION

Lubricants are used in automotive, industrial, marine and aviation applications. They are used to decrease friction and wear, to protect from corrosion, to act as sealants and to affect heat transfer. Most of the lubricants are made from mineral oil and some are synthetic chemicals. Between 5,000 and 10,000 different lubricant formulations are necessary to satisfy more than 90% of all lubricant applications. About 8 million tons of lubricants are consumed every year world over. Out of this about 53% is, collected as waste, thus, endangering our planet. The use of rapidly degradable lubricants instead of the conventional petroleum-derived lubricants could significantly reduce this environmental pollution.

Plant-derived lubricants are renewable and biodegradable. Pure, natural lubricants manufactured by environmentally-safe procedures are gaining more attention in recent years, since they do not contain toxic compounds. Plant-based lubricants are presently used in some applications where there is an environmental risk, for example in marine, forestry and agricultural appliances. However, it is believed that around 90% of lubricants currently used could be replaced by plant-derived lubricants. Some of the advantages of plant-based lubricants include: (1) biodegradability and renewable nature, (2) excellent lubricity, lower friction coefficient than mineral oils, (3) lower evaporation up to 20% less than mineral oils, (4) higher flash point, reducing the risk of fires in applications such as metal cutting, (5) higher viscosity indices, and (6) enhanced performance in some applications. Several studies show that biolubricants have a longer lifespan than mineral oil lubricants. The high production cost of biolubricants (about 5 times more than the petrolubricants) is the main hurdle for their development at the current time. Development of eco-friendly and economically-beneficial routes for preparing plant or vegetable oil-based lubricant base oils is highly desirable.

Fatty acid polyol or long chain alcohol esters have the right composition to be used as lubricant base oils. They are miscible with hydrocarbons. U.S. Pat. No. 8,168,572 B2 discloses the use of the polyols esters in lubricant blend composition. U.S. Pat. No. 8,058,217 B2 teaches that the polyol esters are superior metal working fluids.

These fatty acid esters can be prepared by two different ways: (1) the direct esterification of fatty acids with polyol, and (2) transesterification of fatty acid methyl or ethyl esters (biodiesel) or vegetable oils with polyols. Conventionally, these esterification and transesterification reactions are catalyzed homogeneous mineral acid catalysts. U.S. Pat. No. 7,968,504 B2 teaches the method for preparing fatty acid esters by the reaction of fatty acid ester in the presence of homogeneous phosphoric acid catalyst, with a hydroxyl containing compound. The resulting product is useful as a lubricant, as a heat transfer agent, as a rheological modifier and as a corrosion/moisture inhibitor, among other uses. U.S. Pat. No. 8,101,560 B2 discloses the procedure for preparing lubricant base oil of palm origin, particulary fatty acid monoesters and fatty poly esters by esterifying palm fatty acid with a monohydric or polyhydric alcohol in the presence of a homogeneous acid catalyst.

While homogeneous base catalyst (alkali hydroxides and alkoxides) are efficient for transesterification, they are no good for esterification reactions as the base reacts with fatty acid and forms metallic sops (Masood et al., Appl. Catal. A: Gen., Vol. 425-426, Year 2012, pp. 184-190).

In general, corrosiveness, sensitivity to water, catalyst recovery, environmental hazards and waste control are the serious issues with the homogeneous mineral acid and alkali base catalysts. Solid catalysts have environmental and engineering advantages. They can be easily separated and reused.

References are made to Díaz et al., Micropor. Mesopor. Mater. Vol. 80, Year 2005, pp. 33-42; Pérez-Pariente et al., Appl. Catal. A: Gen. Vol. 254, Year 2003, pp. 173-188; Bossaert et al., J. Catal. Vol. 182, Year 1999, pp. 156-164; and Pouilloux et al., J. Mol. Catal. A: Chem. Vol. 149, Year 1999, pp. 243-254 which disclose the use of zeolites, ion-exchange resins and metal ion-exchanged- or sulfonic acid-functionalized ordered mesoporous silica materials as solid acid catalysts. However, pore-size limitation, loss of activity in presence of by-product water and formation of undesired products are some issues with these solid catalysts. Enzyme catalysts are selective but require longer reaction times (48 hrs and more).

U.S. Pat. No. 7,842,653 and EP 1733788 disclose the use of solid, acid, double metal cyanide catalyst for preparation of lubricants by reacting vegetable oil or fat obtained from animal source with an alcohol at a temperature in the range of 150° C. to 200° C. for a period of 3 to 6 h. Conversion of triglycerides into glycerol in the range 90 to 96 mol % was obtained. Product of this reaction is fatty acid alkyl ester and glycerol. The alcohol used is a normal or branched alcohol, selected from the group consisting of hexanol, heptanol, octanol and their mixture thereof. The product lubricant obtained comprises of $C_{22}$-$C_{28}$ fatty acid alkyl esters. It doesn't disclose the application of this catalyst for reactions with polyols and reaction of fatty acids or fatty acid alkyl esters with mono- or polyhydric alcohols.

U.S. Pat. No. 8,124,801 teaches a process for preparation of fatty acid alkyl esters wherein the process includes contacting fatty acid glycerides with alcohols in the presence of a separable catalyst which includes a metal from Group VIB of the periodic table and an element from Group VA of the periodic table. The process comprises using at least one of the alcohols essentially selected from the group consisting of methanol, ethanol, propanol, butanol, pentanol, octanol, 2-ethylhexanol, decanol, dodecanol and mixture thereof. One of the alcohols has a carbon number ranging from 1 to 50. This process doesn't disclose specifically the use polyols and also conversion of fatty acids or fatty acid methyl or ethyl esters to lubricant base oils. Moreover, relatively long reaction times and high temperature is required.

Article titled, "Synthesis of biolubricants using sulfated zirconia catalysts" by Jinho Oha, Sungeun Yanga, Chanyeon Kima, Inchang Choib, Jae Hyun Kimb, Hyunjoo Leea in Applied Catalysis A: General 455 (2013) 164-171 reports the synthesis of biomass-derived lubricants via esterification, transesterification, and simultaneous reactions of both by using sulfated zirconia catalysts. Soybean oil or free fatty acids derived from soybean oil were used as a biomass-derived resource for the synthesis of biolubricants. Long chain alcohols (carbon number ≤8) or neo-polyols (e.g., 2,2-diethyl-1,3-propanediol, trimethylol propane, pentaery-thritol) were used as co-reactants. The paper further reports that the structure of the alcohol significantly affected the conversion and yield for the esterification with oleic acid.

WO 2012/114357 discloses a process for preparing polyesters by reacting polyols with polycarboxylic acid in presence of heterogeneous, reusable, acid, crystalline, micro-mesoporous double metal cyanide catalyst at moderate temperature and short period of time. Polyolester produced is a hyperbranched polymer having degree of branching in the range 45 to 90% and inherent viscosity in the range 0.02 to 0.1 dL/g.

In view of the importance of polyol and other synthetic esters in industrial applications and drawbacks of prior-art processes which include catalyst deactivation, formation of undesired products, high temperature requirement and long reaction times, it is desirable to have a more efficient, stable, solid catalyst-based esterification/transesterification process for fatty acid polyol or monool esters synthesis. The process of the present invention using solid phosphonate catalyst is highly efficient and overcomes the above-cited deficiencies of the prior-art processes.

OBJECTIVES OF THE INVENTION

Main object of the present invention is to provide an efficient process for preparing fatty acid esters suitable as biodegradable lubricant base oils in the presence of a stable, solid, reusable catalyst.

Another object of the present invention is to provide a catalytic process for preparing biodegradable lubricant base oils wherein the fatty acid esters are formed in a short reaction time (≤1 h) and with high selectivity.

SUMMARY OF THE INVENTION

Accordingly, present invention provides a process for the preparation of fatty acid polyol esters with 100 mol % selectivity as biodegradable lubricant base oils wherein the said process comprising the steps of:

(a) providing recyclable, solid, hydrophobic, acido-basic bifunctional, phosphonate catalyst of molecular formula

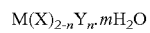

$M(X)_{2-n}Y_n \cdot mH_2O$ wherein X refers to phenyl phosphonate, Y refers to $HPO_4^{2-}$ or $HPO_3^{2-}$, M refers to a metal or metalloid ion preferably taken from the group consisting of Zr, Zn, Cd, Al, Sn, La and Ce, the value of n varies from 0.2 to 1.8 and the value of m varies from 0 to 5, prepared by the known method;

(b) contacting a fatty compound with an alcohol in the ratio ranging between 0.3 to 9 in the presence of 3 to 10% catalyst by weight of fatty compound as provided in step (a);

(c) subjecting the reaction mixture as obtained in step (b) to a temperature in the range of 110 to 200° C. and for a period in the range of 0.5 to 8 h followed by separating the catalyst from liquid products and separating the fatty acid polyol esters from unreacted starting materials.

In an embodiment of the present invention, the fatty compound used is selected from the group consisting of fatty acid or fatty acid methyl ester, fatty acid ethyl ester, vegetable oil or animal fat or their mixture thereof.

In another embodiment of the present invention, the fatty acid in the fatty compound possesses 8 to 24 carbon atoms.

In yet another embodiment of the present invention, alcohol used is monohydric alcohol or a polyol.

In yet another embodiment of the present invention, monohydric alcohol contains 6 to 22 carbon atoms and is a linear or branched compound.

In yet another embodiment of the present invention, the polyol used is with at least two, hydroxyl groups selected preferably from the group consisting of trimethylolpropane, neopentylglycol, pentaerythritol, glycerol and carbohydrate.

In yet another embodiment of the present invention, the fatty acid polyol ester is mono- or di- or triesters of fatty acid—polyols or the mixtures thereof.

In yet another embodiment of the present invention, the reaction is conducted in a batch or continuous fixed-bed reaction mode.

In yet another embodiment of the present invention, the catalyst is shaped into pellets or extrudates when used in a fixed-bed mode.

In yet another embodiment of the present invention, the reaction is carried out optionally under vacuum of 0.01 to 0.9 bar.

In yet another embodiment of the present invention, the solid phosphonate catalyst is hydrophobic with water adsorption capacity in the range of 0-2.5 wt % and contains both acidic and basic sites with their density in the range of 0.1-2 mmol/g.

In yet another embodiment of the present invention, the reaction is carried out optionally in the presence of a miscibility enhancer selected from the group consisting of toluene, tetrahydrofuran, N,N-dimethyl formamide and the mixture thereof.

In yet another embodiment of the present invention, catalyst may be used as-prepared or after calcination at a temperature between 300 and 600° C.

In yet another embodiment of the present invention, the solid phosphonate catalyst is reusable.

In yet another embodiment of the present invention, the selectivity of mono and polyesters is tuned changing the molar ratio of reactants in the reaction.

In yet another embodiment of the present invention, the selectivity of fatty acid esters is 95 to 100% by weight.

DETAILED DESCRIPTION OF THE INVENTION

The present invention discloses a process for preparing biodegradable lubricant base oils. The present invention discloses an improved process for preparing fatty acid esters with 100 mol % selectivity suitable as biodegradable lubricant base oils, comprising contacting a fatty compound with an alcohol in the presence of a solid, hydrophobic, acido-basic bifunctional, phosphonate catalyst having molecular formula:

$$M(X)_{2-n}Y_n \cdot mH_2O$$

where X refers to phosphonate, Y refers to $HPO_4^{2-}$ or $HPO_3^{2-}$, M refers to a metal or metalloid ion preferably taken from the group consisting of Zr, Zn, Cd, Al, Sn, La and Ce, the value of n varies from 0.2 to 1.8 and the value of m varies from 0 to 5, wherein the fatty compound is a fatty acid or fatty acid methyl or ethyl ester or vegetable oil or their mixture thereof and alcohol is a monohydric alcohol with 6 to 22 carbon atoms or a polyol.

The solid phosphonate catalyst of the present invention is highly efficient and could be easily separated from the products for further use. A highly stable and easily separable catalyst, for example, the catalyst of the present invention is advantageous.

The present invention provides a process for the preparation of fatty acid polyol esters with 100 mol % selectivity as biodegradable lubricant base oils wherein the said process comprising the steps of:

a) providing recyclable, solid, hydrophobic, acido-basic bifunctional, phosphonate catalyst of molecular formula $$M(X)_{2-n}Y_n \cdot mH_2O$$

wherein X refers to phenyl phosphonate, Y refers to $HPO_4^{2-}$ or $HPO_3^{2-}$, M refers to a metal or metalloid ion preferably taken from the group consisting of Zr, Zn, Cd, Al, Sn, La and Ce, the value of n varies from 0.2 to 1.8 and the value of m varies from 0 to 5, prepared by the known method;

b) contacting a fatty compound with an alcohol in the ratio ranging between 0.3 to 9 in the presence of 3 to 10% catalyst by weight of fatty compound as provided in step (a);

c) subjecting the reaction mixture as obtained in step (b) to a temperature in the range of 110 to 200° C. and for a period in the range of 0.5 to 8 h followed by separating the catalyst from liquid products and separating the fatty acid polyol esters from unreacted starting materials.

The present invention provides an efficient process for preparing fatty acid esters as biodegradable lubricant base oils wherein the said process comprises the steps of:

(a) contacting a fatty compound with an alcohol in the presence of a solid, hydrophobic, acido-basic bifunctional, phosphonate catalyst having molecular formula:

$$M(X)_{2-n}Y_n \cdot mH_2O$$

where X refers to phenyl phosphonate, Y refers to $HPO_4^{2-}$ or $HPO_3^{2-}$, M refers to a metal or metalloid ion preferably taken from the group consisting of Zr, Zn, Cd, Al, Sn, La and Ce, the value of n varies from 0.2 to 1.8 and the value of m varies from 0 to 5, wherein the fatty compound is a fatty acid or fatty acid methyl or ethyl ester or vegetable oil or animal fat or their mixture thereof, alcohol is a monohydric alcohol with 6 to 22 carbon atoms or a polyol with at least two hydryl groups, the amount of catalyst ranges from 3 to 10% by weight of fatty compound and the molar ratio of fatty compound to alcohol ranges from 0.3 to 9;

(b) subjecting the reaction mixture obtained in step (a) to a temperature in the range of 110 to 200° C. and for a reaction time of 0.5 to 8 hrs (c) separating the catalyst from liquid products and separating the alcohol esters from unreacted starting materials.

It is a feature of the process of present invention that the catalyst is a solid, the reactants are liquids and the reaction takes place in a heterogeneous condition. The solid catalyst can be easily separated from products by centrifugation-filtration/decantation for further reuse.

It is another feature of the process of present invention that the process is eco-friendly, and generates no waste products unlike in the prior art processes using homogeneous catalysts.

It is the unique feature of the catalyst of present invention that they are stable even in the aqueous conditions.

Another unique feature of the present invention is that the reactants are activated at both acidic and basic sites. Simultaneous presence both the acidic and basic sites and hydrophobicity of the catalyst are responsible for its efficient catalytic activity and reusability.

In an embodiment of the present invention, the fatty compound used is selected from the group consisting of fatty acid or fatty acid methyl ester, fatty acid ethyl ester, vegetable oil or animal fat or their mixture thereof.

In another embodiment of the present invention, the fatty acid in the fatty compound possesses 8 to 24 carbon atoms.

In yet another embodiment of the present invention, alcohol used is monohydric alcohol or a polyol.

In yet another embodiment of the present invention, monohydric alcohol contains 6 to 22 carbon atoms and is a linear or branched compound.

In yet another embodiment of the present invention, the polyol used is with at least two hydroxyl groups selected preferably from the group consisting of trimethylolpropane, neopentylglycol, pentaerythritol, glycerol and carbohydrate.

In yet another embodiment of the present invention, the fatty acid polyol ester is mono- or di- or triesters of fatty acid—polyols or the mixtures thereof.

In yet another embodiment of the present invention, the reaction is conducted in a batch or continuous fixed-bed reaction mode.

In yet another embodiment of the present invention, the catalyst is shaped into pellets or extrudates when used in a fixed-bed mode.

In yet another embodiment of the present invention, the reaction is carried out optionally under vacuum of 0.01 to 0.9 bar.

In yet another embodiment of the present invention, the solid phosphonate catalyst is hydrophobic with water adsorption capacity in the range of 0-2.5 wt % and contains both acidic and basic sites with their density in the range of 0.1-2 mmol/g.

In yet another embodiment of the present invention, the reaction is carried out optionally in the presence of a miscibility enhancer selected from the group consisting of toluene, tetrahydrofuran, N,N-dimethyl formamide and the mixture thereof.

In yet another embodiment of the present invention, catalyst may be used as-prepared or after calcination at a temperature between 300 and 600° C.

In yet another embodiment of the present invention, the solid phosphonate catalyst is reusable.

In yet another embodiment of the present invention, the selectivity of mono and polyesters is tuned changing the molar ratio of reactants in the reaction.

In yet another embodiment of the present invention, the selectivity of fatty acid esters is 95 to 100% by weight.

The phosphonate catalysts of the present invention are prepared by the known procedures as described in the references: A. Clearfield et al., J. Sold. State Chem. Vol. 117, Year 1995, pp. 275; J. Don Wang et al., Mater. Chem. Phys. Vol. 35, Year 1993, pp. 208; and K. Nakamura et al., J. Incl. Phenom. Mol. Recog. Chem. Vol. 31, Year 1998, pp. 351.

EXAMPLES

Following examples are given by way of illustration therefore should not be construed to limit the scope of the invention.

Example 1

This example illustrates the preparation of zirconium phenyl phosphonate phospite catalyst of molecular composition: $Zr(C_6H_5PO_3)_{0.95}(HPO_3)_{1.05} \cdot 0.1H_2O$. In a typical synthesis, 1 g of phenyl phosphonic acid and 1.56 g of phosphorous acid were dissolved in 20 ml of water. To this, 2.04 g of zirconyl oxychloride ($ZrOCl_2 \cdot 8H_2O$) dissolved in 5 ml of water was added. The mixture was heated to dryness at 90° C. for 6 hrs. The solid was recovered, washed with 500 ml of water and dried at 90° C. for 16 h. Acidity ($NH_3$-TPD)=0.36 mmol/g, basicity ($CO_2$-TPD)=0.27 mmol/g, water adsorption= 0.5 wt %.

Example 2

This example illustrates the preparation of zirconium phenyl phosphonate phospite catalyst of molecular composition: $Zr(C_6H_5PO_3)_{0.97}(HPO_3)_{1.03} \cdot 0.15H_2O$. In a typical synthesis, 1 g of phenyl phosphonic acid and 1.04 g of phosphorous acid were dissolved in 20 ml of water. To this, 2.04 g of zirconyl oxychloride ($ZrOCl_2 \cdot 8H_2O$) dissolved in 5 ml of water was added. The mixture was heated to dryness at 90° C. for 3 hrs. The solid was recovered, washed with 500 ml of water and dried at 90° C. for 16 h. Acidity ($NH_3$-TPD)=0.27 mmol/g, basicity ($CO_2$-TPD)=0.25 mmol/g, water adsorption= 0.8 wt %.

Example 3

This example illustrates the preparation of zirconium phenyl phosphonate phospite catalyst of molecular composition: $Zr(C_6H_5PO_3)_{0.99}(HPO_3)_{1.01} \cdot 0.4H_2O$. In a typical synthesis, 1 g of phenyl phosphonic acid and 0.52 g of phosphorous acid were dissolved in 20 ml of water. To this, 2.04 g of zirconyl oxychloride ($ZrOCl_2 \cdot 8H_2O$) dissolved in 5 ml of water was added. The mixture was heated to dryness at 90° C. for 3 hrs. The solid was recovered, washed with 500 ml of water and dried at 90° C. for 16 h. Acidity ($NH_3$-TPD)=1.59 mmol/g, basicity ($CO_2$-TPD)=0.21, mmol/g, water adsorption= 2.1 wt %.

Example 4

This example illustrates the preparation of zirconium phenyl phosphonate phospite catalyst of molecular composition: $Zr(C_6H_5PO_3)_{0.5}(HPO_3)_{1.5}$. In a typical synthesis, solution A was prepared by dissolving 4 g of zirconyl oxychloride in 20 ml of water and 9 ml of conc. HF taken in a polyethylene beaker. Solution B was prepared by dissolving 1.06 g of phenyl phosphonic acid and 26.8 g of phosphorous acid in 50 ml of water. Solution A was added to the solution B. Beaker containing solution A was rinsed with 14 ml of water and the contents were added to the reaction mixture. The reaction mixture was heated at 70° C. for 45 h till it got dried. The material was washed with 2 liters of water and dried at 90° C. for 16 h. Acidity ($NH_3$-TPD)=1.7 mmol/g, basicity ($CO_2$-TPD)=0.196 mmol/g, water adsorption=0.1 wt %.

Example 5

This example illustrates the preparation of zirconium phenyl phosphonate phosphate catalyst of molecular composition: $Zr(C_6H_5PO_3)_{0.8}(HPO_4)_{1.2} \cdot 0.5H_2O$. In a typical synthesis, solution A was prepared by dissolving 5.43 g of zirconyl oxychloride in 30 ml of distilled water taken in a polyethylene beaker. To it 12.4 ml of 48% HF was added. Solution B was prepared by disallowing 2.16 g of phenyl phosphonic acid in 45 ml of water. To it 84.6 ml of conc. phosphoric acid was added. Solution A was added slowly at 25° C. to solution B over a period of 1 h. The empty beaker containing solution A was rinsed with 28 ml of water and the contents were added to the above reaction mixture. The combined volume of the reaction mixture was nearly 200 ml. The mixture was heated in oil bath at 70° C. for 2 days till all the solvent got evaporated and solid was formed. The solid was washed with 2 l of water, dried in an oven at 90° C. for 16 h. Acidity ($NH_3$-TPD)=0.4 mmol/g, basicity ($CO_2$-TPD)=0.16 mmol/g, water adsorption=1.5 wt %.

Example 6

This example illustrates the preparation of glyceryl oleate esters in a batch reactor using the as-prepared catalyst described in Example 1. Prior to reaction the as-prepared catalyst of Example 1 was activated at 200° C. for 4 h. Then, 4 g of oleic acid, 0.326 g of glycerol (oleic acid:glycerol molar ratio=4:1) and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by gravity. The product glyceryl oleate esters were isolated and analyzed by HPLC technique.

Example 7

This example illustrates the preparation of glyceryl oleate esters in a batch reactor using the as-prepared catalyst described in Example 1. Prior to reaction the as-prepared catalyst of Example 1 was activated at 200° C. for 4 h. Then, 0.326 g of glycerol, 1 g of oleic acid with oleic acid:glycerol molar ratio=1:1 and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h under vacuum of 0.05 bar. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by treating the liquid with 10 ml of petroleum ether. All the glycerides went into petroleum ether layer. Glycerol remained as a separate layer was separated by decantation. Petroleum ether was distilled out and the product glyceryl oleate esters were isolated and analyzed by HPLC technique.

Example 8

This example illustrates the preparation of glyceryl oleate esters in a batch reactor using the as-prepared catalyst described in Example 2. Prior to reaction the as-prepared catalyst of Example 2 was activated at 200° C. for 4 h. Then, 4 g of oleic acid, 0.32 g of glycerol (oleic acid:glycerol molar ratio=4:1) and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by treating the liquid with 10 ml of petroleum ether. All the glycerides went into petroleum ether layer. Glycerol remained as a separate layer was separated by decantation. Petroleum ether was distilled out and the product glyceryl oleate esters were isolated and analyzed by HPLC technique.

Example 9

This example illustrates the preparation of glyceryl oleate esters in a batch reactor using the as-prepared catalyst described in Example 3. Prior to reaction the as-prepared catalyst of Example 3 was activated at 200° C. for 4 h. Then, 4 g of oleic acid, 0.32 g of glycerol (oleic acid:glycerol molar ratio=4:1) and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by treating the liquid with 10 ml of petroleum ether. All the glycerides went into petroleum ether layer. Glycerol remained as a separate layer was separated by decantation. Petroleum ether was distilled out and the product glyceryl oleate esters were isolated and analyzed by HPLC technique.

Example 10

This example illustrates the preparation of glyceryl oleate esters in a batch reactor using the catalyst described in Example 4. Prior to reaction the catalyst of Example 4 was calcined at 500° C. for 2 h. Then, 4 g of oleic acid, 1.29 g of glycerol (oldie acid:glycerol molar ratio=1:1) and calcined catalyst (3 wt % of oleic acid) were taken in a 100 ml glass, round-bottom flask fitted with a water cooled condenser and placed in a temperature-controlled oil bath. Temperature of the reactor was raised to 180° C. and the reaction was conducted for 5 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by treating the liquid with 10 ml of petroleum ether. All the glycerides went into petroleum ether layer. Glycerol remained as a separate layer was separated by decantation. Petroleum ether was distilled out and the product glyceryl oleate esters were isolated and analyzed by HPLC technique.

Example 11

This example illustrates the preparation of glyceryl oleate esters in a batch reactor using the catalyst described in Example 5. Prior to reaction the catalyst of Example 5 was calcined at 500° C. for 2 h. Then, 4 g of oleic acid, 0.4 g of glycerol (oleic acid:glycerol molar ratio=3.5:1) and calcined catalyst (3 wt % of oleic acid) were taken in a 100 ml glass, round-bottom flask fitted with a water cooled condenser and placed in a temperature-controlled oil bath. Temperature of the reactor was raised to 180° C. and the reaction was conducted for 0.5 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by treating the liquid with 10 ml of petroleum ether. All the glycerides went into petroleum ether layer. Glycerol remained as a separate layer was separated by decantation. Petroleum ether was distilled out and the product glyceryl oleate esters were isolated and analyzed by HPLC technique.

Example 12

This example illustrates the preparation of trimethylolpropane-oleate esters in a batch reactor using the as-prepared catalyst described in Example 1. Prior to reaction the as-prepared catalyst of Example 1 was activated at 200° C. for 4 h. Then, 4 g of oleic acid, 0.48 g of trimethylolpropane, (oleic acid:trimethylolpropane molar ratio of 3:1) and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted trimethylolpropane was separated by gravity. The product trimethyloylpropane-oleate esters were isolated and analyzed by HPLC technique.

Example 13

This example illustrates the preparation of neopentyl glycol-oleate esters in a batch reactor using the as-prepared catalyst described in Example 1. Prior to reaction the as-prepared catalyst of Example 1 was activated at 200° C. for 4 h. Then, 4 g of oleic acid, 0.37 g of neopentyl glycol (oleic acid:neopentyl glycol molar ratio of 4:1) and activated catalyst (3 wt % of oleic acid) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted neopentyl glycol was separated by gravity. The product neopentyl glycol-oleate esters were isolated and analyzed by HPLC technique.

Example 14

This example illustrates the preparation of glyceryl oleate esters in a batch reactor using the as-prepared catalyst described in Example 1. Prior to reaction the as-prepared catalyst of Example 1 was activated at 200° C. for 4 h. Then, 4 g of methyl oleate, 0.31 g glycerol with methyl oleate:glycerol molar ratio=4:1, tetrahydrofuran-water (1:1 wt/wt) (10 wt % of methyl oleate) and activated catalyst (3 wt % of methyl oleate) were taken in a 100 ml glass, round-bottom flask fitted with a water cooled condenser and placed in a temperature-controlled oil bath. Temperature of the reactor was raised to 180° C. and the reaction was conducted for 1 h. Then, the solid catalyst was separated from the reaction mixture by centrifugation/filtration. Unreacted glycerol was separated by treating the liquid with 10 ml of petroleum ether. All the glycerides went into petroleum ether layer. Glycerol and water remained as a separate layer was separated by decantation. Petroleum ether and THF were distilled out and the product glyceryl oleate esters were isolated and analyzed by HPLC technique.

Example 15

This example illustrates the preparation of glyceryl fish oil esters in a batch reactor using the as-prepared catalyst described in Example 1. Prior to reaction the as-prepared catalyst of Example 1 was activated at 200° C. for 4 h. Then, 4 g of fish oil methylate, 0.44 g of glycerol with fish oil methylate:glycerol molar ratio=3:1, tetrahydrofuran-water (1:1 wt/wt) (10 wt % of fish oil methylate) and activated catalyst (3 wt % of fish oil methylate) were taken in a 100 ml glass, round-bottom flask fitted with a water cooled condenser and placed in a temperature-controlled oil bath. Temperature of the reactor was raised to 190° C. and the reaction was conducted for 8 h. Then, the solid catalyst was separated from the reaction mixture by centrifugation/filtration. Unreacted glycerol was separated by treating the liquid with 10 ml of petroleum ether. All the glycerides went into petroleum ether layer. Glycerol and water remained as a separate layer was separated by decantation. Petroleum ether and THF were distilled out and the product glyceryl fish oil esters were isolated and analyzed by HPLC technique.

Example 16

This example illustrates the preparation of glyceryl soy oil esters in a batch reactor using the as-prepared catalyst described in Example 1. Prior to reaction the as-prepared catalyst of Example 1 was activated at 200° C. for 4 h. Then, 4 g of soy oil methyl ester, 0.413 g of glycerol with soy oil methyl ester:glycerol molar ratio=3:1, tetrahydrofuran-water (1:1 wt/wt) (10 wt % of soy oil methyl ester) and activated catalyst (3 wt % of oleic acid) were taken in a 100 ml glass, round-bottom flask fitted with a water cooled condenser and placed in a temperature-controlled oil bath. Temperature of the reactor was raised to 190° C. and the reaction was conducted for 8 h. Then, the solid catalyst was separated from the reaction mixture by centrifugation/filtration. Unreacted glycerol was separated by treating the liquid with 10 ml of petroleum ether. All the glycerides went into petroleum ether layer. Glycerol and water remained as a separate layer was separated by decantation. Petroleum ether and THF were distilled out and the product glyceryl soy oil esters were isolated and analyzed by HPLC technique.

Example 17

This example illustrates the preparation of trimethylolpropane caprylate esters in a batch reactor using the as-prepared catalyst described in Example 1. Prior to reaction the as-prepared catalyst of Example 1 was activated at 200° C. for 4 h. Then, 4 g of caprylic acid, 1.24 g of trimethylolpropane (caprylic acid:trimethylolpropane molar ratio=3:1) and activated catalyst (5 wt % of oleic acid) were taken in a 100 ml glass, round-bottom flask fitted with vacuum distillation unit and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Caprylic acid conversion was estimated from the acid value of the product. Unreacted trimethyloylpropane was separated by gravity. The product trimethylolpropane caprylate esters were isolated and analyzed by HPLC technique.

Example 18

This example illustrates the recyclability of the catalyst in the preparation of glyceryl oleate esters in a batch reactor. The catalyst separated after use in EXAMPLE 6 was used in this reaction without subjecting it to any treatment. 4 g of oleic acid, 0.32 g of glycerol (oleic acid:glycerol molar ratio=4:1) and used catalyst (5 wt % of oleic acid) were taken in a 100 ml glass, round-bottom flask fitted with vacuum distillation unit and placed in a temperature-controlled oil bath. Temperature of the reactor was raised to 180° C. and the reaction was conducted for 1 h. Then, the solid catalyst was separated from the reaction mixture by centrifugation/filtration. Acid value of the liquid product was determined by titrating it with 0.1 N NaOH and using 1,10-phenanthrolein as indicator. Oleic acid conversion was estimated from the acid value of the product. Unreacted glycerol was separated by gravity. The product glyceryl oleate esters were isolated and analyzed by HPLC technique.

Example 19

This example illustrates the preparation of glyceryl oleate esters in a fixed-bed reactor. The catalyst of Example 1 was shaped into extrudates of 1/24" diameter. It was loaded into a 50 cc fixed-bed reaction. Oleic acid and glycerol (oleic acid:glycerol molar ratio=4:1) were pumped at a weight hourly space velocity of 0.4 with respect to oleic acid into the catalytic reactor heated at 180° C. Acid value of the liquid product was determined by titrating it with 0.1 N NaOH and using 1,10-phenanthrolein as indicator. Oleic acid conversion was estimated from the acid value of the product. Unreacted glycerol was separated by gravity. The product glyceryl oleate esters were isolated and analyzed by HPLC technique.

Example 20

This example illustrates the preparation of octyl oleate esters in a batch reactor using the as-prepared catalyst described in Example 1. Prior to reaction the as-prepared catalyst of Example 1 was activated at 200° C. for 4 h. Then, 4 g of oleic acid, 5.53 g of octanol with oleic acid:octanol molar ratio=1:3, and activated catalyst (5 wt % of oleic acid) were taken in a 100 ml glass, round-bottom flask fitted with a water cooled condenser and placed in a temperature-controlled oil bath. Temperature of the reactor was raised to 180° C. and the reaction was conducted for 8 h. Then, the solid catalyst was separated from the reaction mixture by centrifugation/filtration. Unreacted octanol was distilled out. Unreacted oleic acid was analyzed by titrimetric method and selectivity of octyl oleate ester was determined by HPLC technique. Oleic acid conversion=95 mol %. Octyl oleate ester selectivity=97 mol %.

Example 21

This example illustrates the preparation of octyl oleate esters in a batch reactor using the as-prepared catalyst described in Example 1. Prior to reaction the as-prepared catalyst of Example 1 was activated at 200° C. for 4 h. Then, 4 g of methyl oleate, 5.25 g of octanol with methyl oleate:octanol molar ratio=1:3, and activated catalyst (5 wt % of methyl oleate) were taken in a 100 ml glass, round-bottom flask fitted with a water cooled condenser and placed in a temperature-controlled oil bath. Temperature of the reactor was raised to 180° C. and the reaction was conducted for 8 h. Then, the solid catalyst was separated from the reaction mixture by centrifugation/filtration. Unreacted octanol was distilled out. Conversion of methyl oleate and selectivity of octyl oleate ester were determined by HPLC technique. Methyl oleate conversion=91 mol %. Octyl oleate ester selectivity=98 mol %.

Example 22

This example illustrates the preparation of octyl esters of fatty acids derived from soybean oil in a batch reactor using the as-prepared catalyst described in Example 1. Prior to reaction the as-prepared catalyst of Example 1 was activated at 200° C. for 4 h. Then, 4 g of soybean oil, 6.70 g of octanol with soybean oil:octanol molar ratio=1:9, and activated catalyst (5 wt % of soybean oil) were taken in a 100 ml glass, round-bottom flask fitted with a water cooled condenser and placed in a temperature-controlled oil bath. Temperature of the reactor was raised to 190° C. and the reaction was conducted for 8 h. Then, the solid catalyst was separated from the reaction mixture by centrifugation/filtration. Unreacted octanol was distilled out. Conversion of soybean oil and selectivity of octyl esters were determined by HPLC technique. Methyl oleate conversion=89 mol %. Octyl ester selectivity=90 mol % and mono-+ di-+ triglyceride esters selectivity=10 mol %.

The results of the reactions exemplified in Examples 6-19 are listed in Table 1.

TABLE 1

| | Catalytic activity data | | | | | |
|---|---|---|---|---|---|---|
| Example No. | Acid or Ester conversion (mol %) | Polyol esters selectivity (mol %) | | | Selectivity of overall polyol esters (mol %) | Polyol esters yield (mol %) |
| | | Mono | Di | Tri | | |
| 6 | 66.0 | 7.7 | 66.1 | 26.3 | 100 | 66 |
| 7 | 79.0 | 68.9 | 30.7 | 0.3 | 100 | 79 |
| 8 | 63.0 | 11.8 | 71.7 | 17.0 | 100 | 63 |
| 9 | 53.0 | 58.1 | 39.8 | 2.1 | 100 | 53 |
| 10 | 89.9 | 58.0 | 38.5 | 3.5 | 100 | 89.9 |
| 11 | 18.7 | 84.8 | 14.8 | 0.4 | 100 | 18.7 |
| 12 | 66.0 | 9.0 | 74.6 | 16.4 | 100 | 66.0 |
| 13 | 60.0 | 45.8 | 34.0 | 20.2 | 100 | 60.0 |
| 14 | 39.0 | 55.0 | 39.3 | 3.7 | 100 | 39.0 |
| 15 | 39.7 | 55.2 | 39.0 | 3.5 | 100 | 39.7 |
| 16 | 17.4 | 69.8 | 30.2 | 0 | 100 | 17.4 |
| 17 | 100.0 | 35.5 | 41.9 | 22.6 | 100 | 100 |
| 18 | 66.0 | 7.7 | 66.1 | 26.2 | 100 | 66 |
| 19 | 50.0 | 49.0 | 32.9 | 17.0 | 96 | 48 |

Advantages of the Invention

Advantages of instant invention are as following:
i. Heterogeneous, bi-functional, hydrophobic catalyst-based process;
ii. Reusable catalyst process;
iii. Eco-friendly process;
iv. Alcohol esters selectivity of 95 to 100% by weight;
v. Reaction can be carried out in batch or continuous fixed-bed reaction mode;
vi. No side products such as ethers formed.

We claim:
1. A process for preparation of fatty acid esters with 100 mol % selectivity as biodegradable lubricant base oils wherein the said process comprising the steps of:
(a) providing recyclable, solid, hydrophobic, acido-basic bifunctional, phosphonate catalyst of molecular formula

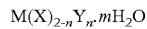

$$M(X)_{2-n}Y_n \cdot mH_2O$$

wherein X refers to phenyl phosphonate, Y refers to $HPO_4^{2-}$ or $HPO_3^{2-}$, M refers to a metal ion, said metal being of Zr, the value of n varies from 0.2 to 1.8 and the value of m varies from 0 to 5;
(b) contacting a fatty compound with an alcohol in a molar ratio ranging between 0.3 and 9 in presence of 3 to 10% catalyst by weight of fatty compound as provided in step (a); and
(c) subjecting the reaction mixture as obtained in step (b) to a temperature in the range of 110 to 200° C. and for a period in the range of 0.5 to 8 h followed by separating the catalyst from liquid products and separating the fatty acid esters from unreacted starting materials.
2. The process according to step (b) of claim 1, wherein the fatty compound used is selected from the group consisting of fatty acid or fatty acid methyl ester, fatty acid ethyl ester, vegetable oil or animal fat or their mixture thereof.
3. The process according to claim 2, wherein the fatty acid in the fatty compound possesses 8 to 24 carbon atoms.
4. The process according to claim 1, wherein alcohol used is a linear or branched monohydric alcohol containing 6 to 22 carbon atoms or a polyol with at least two hydroxyl groups selected from the group consisting of trimethylolpropane, neopentylglycol, pentaerythritol, glycerol and carbohydrate.

5. The process according to claim 1, wherein the fatty acid ester is mono- or di- or triesters or the mixtures thereof of fatty acid and alcohol.

6. The process according to claim 1, wherein the reaction is conducted in a batch or continuous fixed-bed reaction mode.

7. The process according to claim 1, wherein the reaction is carried out under vacuum of 0.01 to 0.9 bar.

8. The process according to claim 1, wherein the catalyst is hydrophobic with water adsorption capacity in the range of 0-2.5 wt % and contains both acidic and basic sites with their density in the range of 0.1-2 mmol/g.

9. The process according to claim 1, wherein the reaction is carried out in the presence of a miscibility enhancer selected from the group consisting of toluene, tetrahydrofuran, N,N-dimethyl formamide and the mixture thereof.

10. The process as claimed in claim 1, wherein catalyst is used as-prepared or after calcining at a temperature between 300 and 600° C.

* * * * *